(12) United States Patent
Lee et al.

(10) Patent No.: US 12,103,953 B2
(45) Date of Patent: Oct. 1, 2024

(54) FGF2 POLYPEPTIDE WITH IMPROVED TEMPERATURE STABILITY AND PROTEASE RESISTANCE AND USE THEREOF

(71) Applicants: Korea Institute of Ocean Science & Technology, Busan (KR); Kiweon Cha, Cheongju-si (KR)

(72) Inventors: Jung-Hyun Lee, Busan (KR); Hyung-Soon Yim, Seoul (KR); Young Jun An, Ansan-si (KR); Kyeong Won Lee, Busan (KR); Ye Eun Jeong, Busan (KR); Kiweon Cha, Cheongju-si (KR); Won Kyu Lee, Goyang-si (KR); Jurang Woo, Sejong (KR)

(73) Assignees: KOREA INSTITUTE OF OCEAN SCIENCE TECHNOLOGY, Busan (KR); Kiweon Cha, Cheongju-si (KR)

( * ) Notice: Subject to any disclaimer, the term of this patent is extended or adjusted under 35 U.S.C. 154(b) by 300 days.

(21) Appl. No.: 17/779,210

(22) PCT Filed: Nov. 16, 2020

(86) PCT No.: PCT/KR2020/016065
§ 371 (c)(1),
(2) Date: May 24, 2022

(87) PCT Pub. No.: WO2021/107473
PCT Pub. Date: Jun. 3, 2021

(65) Prior Publication Data
US 2023/0076299 A1    Mar. 9, 2023

(30) Foreign Application Priority Data

Nov. 25, 2019 (KR) .......... 10-2019-0152362
Oct. 7, 2020 (KR) .......... 10-2020-0129526

(51) Int. Cl.
*C07K 14/50* (2006.01)
*C12N 5/0735* (2010.01)

(52) U.S. Cl.
CPC ............ *C07K 14/50* (2013.01); *C12N 5/0606* (2013.01)

(58) Field of Classification Search
None
See application file for complete search history.

(56) References Cited

U.S. PATENT DOCUMENTS

| | | | |
|---|---|---|---|
| 9,169,309 B2 | 10/2015 | Jeong | |
| 10,336,799 B2 * | 7/2019 | Nolle ................... | C07K 14/503 |
| 2005/0148511 A1 | 7/2005 | Bogin et al. | |
| 2010/0298220 A1 | 11/2010 | Blaber et al. | |
| 2015/0284443 A1 * | 10/2015 | Nolle ................... | C07K 14/503 |
| | | | 435/405 |
| 2017/0291931 A1 | 10/2017 | Evans et al. | |
| 2018/0319857 A1 | 11/2018 | Evans et al. | |
| 2019/0284252 A1 | 9/2019 | Thallapuranam et al. | |
| 2020/0270320 A1 | 8/2020 | Dvorak et al. | |

FOREIGN PATENT DOCUMENTS

| | | |
|---|---|---|
| CN | 108779158 | 11/2018 |
| EP | 0298723 | 1/1989 |
| EP | 2930181 | 10/2015 |
| EP | 3380508 | 10/2018 |
| JP | 2017-140032 | 8/2017 |
| JP | 2019-500414 | 1/2019 |
| KR | 10-2009-0083062 | 8/2009 |
| KR | 10-2016-0118784 | 10/2016 |
| KR | 10-2018-0080335 | 7/2018 |
| KR | 1020210044749 | 4/2021 |
| KR | 10-2021-0152507 | 12/2021 |
| WO | 1995-008630 | 3/1995 |
| WO | 2004-069298 | 8/2004 |
| WO | 2012-158244 | 11/2012 |
| WO | 2016-195157 | 12/2016 |
| WO | 2017-089016 | 6/2017 |
| WO | 2018-016814 | 1/2018 |

OTHER PUBLICATIONS

Dvorak et al. Computer-assisted engineering of hyper stable fibroblast growth factor 2. Biotech. Bioeng. 115: 850-862, 2018.*
Motomura et al. An FGF1: FGF2 chimeric growth factor exhibits universal FGF receptor specificity, enhanced stability and augmented activity useful for epithelial proliferation and radioprotection. Biochim. Biophys. Acta 1780: 1432-1440, 2008.*
Benington et al. Fibroblast Growth Factor 2—A Review of Stabilisation Approaches for Clinical Applications. Pharmaceutics 2020, 12, 508; doi:10.3390/pharmaceutics 12060508.*
Gasparian et al. Overexpression in Escherichia coli and Purification of Human Fibroblast Growth Factor (FGF-2). Biochem. (Moscow) 74(2): 221-225, 2009.*
Guokai Chen et al., "Thermal Stability of Fibroblast Growth Factor Protein Is a Determinant Factor in Regulating Self-Renewal, Differentiation, and Reprogramming in Human Pluripotent Stem Cells", Stem Cells, 2012;30:623-630.
Boris Greber et al., "Fibroblast Growth Factor 2 Modulates Transforming Growth Factor beta Signaling in Mouse Embryonic Fibroblasts and Human ESCs (hESCs) to Support hESC Self-Renewal", Stem Cells25, 455-464.
Livia Eiselleova et al., "A Complex Role for FGF-2 in Self-Renewal, Survival, and Adhesion of Human Embryonic Stem Cells", Stem Cells27, 1847-1857.

(Continued)

*Primary Examiner* — Christine J Saoud
(74) *Attorney, Agent, or Firm* — LEX IP MEISTER, PLLC (57) ABSTRACT

Provided is a polypeptide having FGF2 activity and improved temperature stability and protease resistance. The polypeptide includes at least one substitution selected from a substitution of aspartic acid (D) with glutamic acid (E) at position 28, a substitution of cysteine (C) with isoleucine (I) or leucine (L) at position 78, or a substitution of cysteine (C) with isoleucine (I) or tryptophan (W) at position 96 in SEQ ID NO: 1.

4 Claims, 5 Drawing Sheets

Specification includes a Sequence Listing.

(56) References Cited

OTHER PUBLICATIONS

The International Stem Cell Initiative, "Characterization of human embryonic stem cell lines by the International Stem Cell Initiative", Nat Biotechnol 25, 803-816.

Miriama Kruta' et al., "Mutation Frequency Dynamics in HPRT Locus in Culture-Adapted Human Embryonic Stem Cells and Induced Pluripotent Stem Cells Correspond to Their Differentiated Counterparts", Stem Cells and Development 23, 2443-2454.

Wu Xiao-Ping et al., "Study on Expression , Purification , and Stability of Recombinant Human Basic Fibroblast Growth Factor Mutant, [ Ser69, 87] hbFGF", Journal of China Pharmaceutical University, 2005, 36(2):168 -172.

Yu Suzuki, "Strategy of the proline theory for—heat resistance of proteins", Chemistry and biological, 1995, vol. 33, No. 4, pp. 218-223.

Tomoko Sotomatsu-Niwa et al., "Evaluation of the hydrophobic parameters of the amino acid side chains of peptides and their application in QSAR and conformational studies", Journal of Molecular Structure: THEOCHEM, vol. 392, Mar. 31, 1997, pp. 43-54.

* cited by examiner

SEQUENCE LISTING

```
<160> NUMBER OF SEQ ID NOS: 1

<210> SEQ ID NO 1
<211> LENGTH: 155
<212> TYPE: PRT
<213> ORGANISM: Artificial Sequence
<220> FEATURE:
<223> OTHER INFORMATION: Synthetic_Fibroblast Growth Factor 2

<400> SEQUENCE: 1

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
```

```
65                  70                  75                  80
Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155
```

FGF2 POLYPEPTIDE WITH IMPROVED TEMPERATURE STABILITY AND PROTEASE RESISTANCE AND USE THEREOF

TECHNICAL FIELD

The present disclosure relates to an FGF2 polypeptide having improved temperature stability and protease resistance, and a use thereof.

BACKGROUND ART

FGF (Fibroblast Growth Factor) is a factor that plays an important role in regulating cell growth, proliferation, and differentiation. Various types of FGFs are generated to maintain the function of each tissue in the human body, and they perform unique functions in cell differentiation and proliferation. However, as aging progresses, a concentration of FGFs in each tissue, such as the skin, is gradually lowered, and accordingly cell regeneration and division functions are weakened, so that wrinkles may be formed in the skin and elasticity may be reduced.

Among the various FGFs, FGF2 (Fibroblast Growth Factor 2) mainly consists of 155 amino acids and has a molecular weight of about 18 kDa. FGF2 has broad mitotic and cell survival activity and serves as a potent mediator in wound healing, angiogenesis, and growth of the nervous system.

Accordingly, FGF2 is not only developed as a medicine for promoting angiogenesis, wound healing, cartilage or bone formation, and neurogenesis, but is also widely used as a cosmetic raw material for skin regeneration, wrinkle removal, or elasticity increase. In addition, FGF2 has a function of maintaining cells in a pluripotent state and thus is added as a major factor to a culture medium for human pluripotent stem cells (PSC).

As described above, it is reported that FGF2, which has various functions in the human body, is thermodynamically less stable than epithelial growth factor (EGF), insulin-like growth factor (IGF), and vascular endothelial growth factor (VEGF). In addition, FGF2 has a problem of being easily cleaved by proteases. Accordingly, in order to suitably apply FGF2 for industrial use, it is essential to ensure thermodynamic stability and/or protease resistance of FGF2.

DISCLOSURE

Technical Problem

The present disclosure provides an FGF2 polypeptide having improved temperature stability and protease resistance.

The present disclosure provides a pharmaceutical or cosmetic composition including an FGF2 polypeptide having improved temperature stability and protease resistance.

The present disclosure is to provide a human pluripotent stem cell culture medium including the FGF2 polypeptide having improved temperature stability and protease resistance.

Technical Solution

An FGF2 polypeptide with improved temperature stability according to embodiments includes at least one substitution selected from a substitution of aspartic acid (D) with glutamic acid (E) at position 28, a substitution of cysteine (C) with isoleucine (I) or leucine (L) at position 78, or a substitution of cysteine (C) with isoleucine (I) or tryptophan (W) at position 96 in SEQ ID NO: 1, and is a polypeptide having improved temperature stability and intrinsic activity of FGF2.

The composition according to embodiments includes a polypeptide having improved temperature stability and protease resistance, and a pharmaceutically or cosmetically acceptable carrier.

The human pluripotent stem cell culture medium according to embodiments includes a polypeptide having improved temperature stability and protease resistance as an active ingredient.

Advantageous Effects

The FGF2 polypeptide according to embodiments exhibits improved temperature stability and protease resistance compared to the wild-type human FGF2 polypeptide after manufacture.

The polypeptide having improved temperature stability and protease resistance may maintain activity during distribution and storage, unlike existing wild human FGF2 products. Therefore, it can be used as an active ingredient in a pharmaceutical or cosmetic composition. In addition, activity inducing undifferentiated proliferation may be maintained for a long period of time compared to wild-type FGF2 when used as an active ingredient of a human pluripotent stem cell culture medium.

MODE FOR INVENTION

Hereinafter, the embodiments will be described in detail so that those skilled in the art can easily perform the embodiments. The embodiments may be implemented in various different forms, and the present disclosure is not limited only to the specific embodiments described herein.

Unless the definition of some terms used in the present disclosure is defined otherwise below, all technical and scientific terms used herein have the same meaning as commonly understood by one of ordinary skill in the art to which the present invention belongs.

The techniques and processes described in this disclosure are generally performed according to conventional methods, which are presented throughout this application. In general, nomenclatures and experimental procedures in molecular biology, biochemistry, analytical chemistry, and cell culture used in this disclosure are well known in the art and are the same as those commonly used.

Variants

The present disclosure provides a FGF2 polypeptide that is thermally stabilized by site-specific mutagenesis. In the present disclosure, a mutation is produced by site-specific mutagenesis after rationally predicting the most optimal amino acid at a new position that is not known previously through bioinformation analysis and protein design using a computer.

In the present disclosure, the term "wild-type" refers to native FGF2 having the most common amino acid sequence among members of the species. In the present disclosure, wild-type FGF2 is a human FGF2 that is an 18 kDa protein having a length of 155 amino acids (SEQ ID NO: 1).

In the present disclosure, "fragment" refers to a functional fragment of an FGF2 polypeptide having FGF2 activity. In addition, it refers to a functional fragment of a FGF2 polypeptide having 85% or more sequence identity with the sequence of SEQ ID NO: 1. The fragment of the FGF2 polypeptide may also have at least one or more substitutions according to the invention. Sequence identity of at least 96%, 97%, 98%, 99%, or 100% is preferred. The fragment is intended as a polypeptide consisting only of a part of the intact polypeptide sequence and structure, and may include C-terminal or N-terminal deletion of the variant. The functional fragment may have a cell binding region and a heparin binding segment of the FGF2 protein of interest according to the present invention.

In the present disclosure, "sequence identity" means that the same amino acid residues are found in the FGF2 polypeptide according to the present invention as described above. When the specified contiguous segments of the amino acid sequence of the FGF2 polypeptide are aligned and compared with the specific amino acid sequence corresponding to the reference molecule, the wild-type human FGF2 polypeptide is used as a reference. The percentage (%) of sequence identity is calculated by measuring the number of positions in which the same amino acid residue exists in both sequences, dividing this by the total number of positions in the segment compared with the reference molecule, and multiplying this by 100 to calculate the percentage (%) of sequence identity. Sequence alignment methods are well known in the art.

The reference sequence as used herein refers to the specifically corresponding wild-type human FGF2 protein. For example, in mammalian species such as mice, rats, rabbits, primates, pigs, dogs, cattle, horses, and humans, FGF2 is highly conserved and exhibits greater than 85% sequence identity across a wide range of species. It is desirable that the sequence identity is at least 96%, 97%, 98%, or 99% or more, or 100%. A person of ordinary skill in the art may appreciate that the remaining 15% or less of the amino acids in the full length of the FGF2 protein according to the present invention may be variable, for example, using other sources of FGF2 species or due to suitable non-FGF2 peptide sequences generally known in the art, or addition of a tag. The FGF2 protein according to an embodiment of the present invention having 85% or more identity to wild-type FGF2 is unlikely to contain similar proteins other than FGF2, since other members of the FGF family generally have very low sequence identity.

The present inventors confirmed that position 28 or position 137 in wild-type human FGF2 is a position associated with thermal stability and/or protease resistance of the FGF2 polypeptide. Further, it was confirmed that the cysteine at position 78 or 96 among the cysteines exposed on the surface of FGF2 is a position associated with thermal stability and/or protease resistance.

Changing to the most appropriate amino acid at a position associated with thermal stability and/or protease resistance requires an inventor's inventive step.

The present inventors confirmed that thermal stability can be improved by substituting aspartic acid (D) with glutamic acid (E) at position 28.

In addition, it was confirmed that thermal stability can be further improved by substituting serine (S) at position 137 with proline (P).

In addition, it was confirmed that thermal stability can be further improved by substituting at both position 28 and position 137.

In the case of positions 78 and 96, a stabilization comparison was performed after 19 mutations through SDM ((http://mari.bioc.cam.ac.uk, University of Cambridge) and Discovery Studio 2019 (BIOVIA).

In the case of position 78, in the SDM analysis, the predicted value (predicted pseudo ΔG) was 0.33, which was the highest, and in the case of mutation with isoleucine (I) in Discovery Studio, it was predicted that the mutation energy change value (kcal/mol) was −1.20, which was predicted to be the most stable.

In the case of position 96, in the SDM analysis, the predicted value (predicted pseudo ΔG) was 0.19, which was the highest, and in the case of mutation with tryptophan (W) in Discovery Studio, the mutation energy change value (kcal/mol) was-0.39, which was predicted to be the most stable.

U.S. Pat. No. 9,169,309, US2017-0291931, EP3380508, US 20180319857, etc. disclose that cysteine at position 78 is substituted with serine (S) or tyrosine (Y), or cysteine at position 96 is substituted with serine (S), tyrosine (Y), threonine (T), asparagine (N), and the like. In the case of these substituted amino acids, the majority are hydrophilic and uncharged amino acids, whereas in the present disclosure, the substituted amino acids are hydrophobic amino acids and may be viewed as a category that cannot be easily predicted from the prior art.

Accordingly, a possible variant in the present disclosure may be any one of various variants disclosed in Table 1.

TABLE 1

| # | Variant |
|---|---------|
| 1 | (D28E) |
| 2 | (C78I) |
| 3 | (C78L) |
| 4 | (C96I) |
| 5 | (C96W) |
| 6 | (S137P) |
| 7 | (D28E, C78I) |
| 8 | (D28E, C78L) |

TABLE 1-continued

| # | Variant |
|---|---|
| 9 | (D28E, C96I) |
| 10 | (D28E, C96W) |
| 11 | (D28E, C137P) |
| 12 | (C78I, C96I) |
| 13 | (C78I, C96W) |
| 14 | (C78L, C96I) |
| 15 | (C78L, C96W) |
| 16 | (C78I, S137P) |
| 17 | (C78L, S137P) |
| 18 | (C96I, S137P) |
| 19 | (C96W, S137P) |
| 20 | (D28E, C78I, C96I) |
| 21 | (D28E, C78I, C96W) |
| 22 | (D28E, C78L, C96I) |
| 23 | (D28E, C78L, C96W) |
| 24 | (D28E, C78I, S137P) |
| 25 | (D28E, C78L, S137P) |
| 26 | (D28E, C96I, S137P) |
| 27 | (D28E, C96W, S137P) |
| 28 | (C78I, C96I, S137P) |
| 29 | (C78I, C96W, S137P) |
| 30 | (C78L, C96I, S137P) |
| 31 | (C78L, C96W, S137P) |
| 32 | (D28E, C78I, C96I, S137P) |
| 33 | (D28E, C78I, C96W, S137P) |
| 34 | (D28E, C78L, C96I, S137P) |
| 35 | (D28E, C78L, C96W, S137P) |

Among the above various variants, mutation at one position may also improve thermal stability and/or protease resistance, but two or more mutations may be desirable for improving thermal stability and/or protease resistance. Furthermore, 3 to 4 mutations may be more desirable for improving thermal stability and/or protease resistance. In general, a coding gene of FGF2 is cloned and then expressed in a transformed organism, preferably in a microorganism. A host organism expresses a foreign gene to produce FGF2 under expression conditions. In addition, a synthetic recombinant FGF2 may be made in eukaryotes, for example, yeasts or human cells. FGF2 may be in the form of 146 amino acids, 153 to 155 amino acids, or a mixture thereof depending on a method of producing recombinants. The description provided in the present application for the first time demonstrates that some changes in wild-type FGF2 construct FGF2 mutations with higher temperature stability and a longer half-life than the wild-type protein. The FGF2 protein of the present invention used to insert the substitutions described herein, as long as it meets criteria specified herein, that is, is thermally stabilized while retaining desired biological activity of the wild-type FGF2, may be derived from any mammal such as mice, rats, rabbits, primates, pigs, dogs, cattle, horses, humans, etc. Preferably, the FGF2 protein of interest is derived from a human source. However, regarding an amino acid sequence SEQ ID No: 1 of the human FGF2 protein, which is used as a comparative reference, all biological active variants for mammalian FGF2 having greater than or equal to 85% and most preferably, greater than or equal to about 96%, greater than or equal to 97%, greater than or equal to 98%, or greater than or equal to 99% of sequence identity may be used in the present invention.

In some embodiments, the stable FGF2 polypeptides according to the present invention may further include a tag or a sequence, which may be used to facilitate detection, purification, tagging to specific tissues or cells, improved stability, extended activity, improved expression, etc., in addition to any additional FGF peptide known in the art.

Pharmaceutical and Cosmetic Compositions

The various variants disclosed in Table 1 may be provided as pharmaceutical and/or cosmetic compositions together with a pharmaceutically or cosmetically acceptable carrier.

The various variants disclosed in Table 1 may be administered to a subject in need of promoting angiogenesis, wound healing, cartilage or bone formation, or neurogenesis, or a subject in need of improving skin conditions such as wrinkle improvement, skin elasticity improvement, skin aging prevention, hair loss prevention or hair growth promotion, skin moisture improvement, age spot removal, or acne treatment. The various variants disclosed in Table 1 may be administered in the "native" form, or, if desired, in the form of salts, esters, amides, prodrugs, derivatives, and the like, but the salts, esters, amides, prodrugs, or derivatives may be selected from substances that are pharmacologically compatible, that is, effective for the method(s). Salts, esters, amides, prodrugs, and other derivatives of peptides are known to those skilled in the art of synthetic organic chemistry, and may be prepared using, for example, standard known procedures.

The various variants disclosed in Table 1 may be formulated into transdermally-administered products, for example, aerosols, creams, serums, and patches for subcutaneous, parenteral, topical, oral, nasal (or otherwise inhaled), rectal, or topical administration. The composition may be administered in various unit dosage forms depending on the method of administration. Suitable unit dosage forms may include, but are not limited to, powders, tablets, pills, capsules, lozenges, suppositories, patches, nasal sprays, injections, implantable sustained release formulations, lipid complexes, and the like.

When the various variants disclosed in Table 1 are combined with a cosmetically acceptable carrier to form a cosmetic composition, fillers (e.g., hyaluron fillers, polymethylmethacrylate (PMMA) microspheres, and collagen fillers), etc. may be additionally included. The composition may preferably be for topical, subcutaneous, or transdermal administration.

The composition may be an injectable composition.

The composition may further include collagen (e.g., bovine, porcine, or human collagen) and hyaluronic acid. The collagen may be synthetic collagen, and the hyaluronic acid may be a chicken meal or a fermentation product of a microorganism.

The composition may further include an anesthetic (e.g., lidocaine).

The composition may be a skin cream (e.g., a face cream).

The composition may be a liquid chemical formulation in the form of a serum or toner.

The composition may be a semi-solid preparation in a gel state.

The pharmaceutically acceptable carrier includes those listed in other generally-recognized pharmacopeias which are approved by a federal or state regulatory agency or used in U.S. pharmacopeia or in animals, particularly, in humans or animals, and more particularly, in humans. The "carrier" means, for example, a diluent, adjuvant, excipient, auxiliary agent, or vehicle which is administered with one or more peptides described herein.

The pharmaceutically acceptable carrier may contain, for example, at least one physiologically acceptable compound that acts to stabilize the composition or increase or decrease absorption of the various variants disclosed in Table 1. The physiologically acceptable compound may include, for example, carbohydrates such as glucose, sucrose, or dextran, antioxidants such as ascorbic acid or glutathione, chelating agents, low molecular weight proteins, protective and absorption enhancers such as lipids, compounds that reduce the clearance or hydrolysis of the peptide, or other excipients, stabilizers, and/or pH adjusting buffers.

Other physiologically acceptable compounds, particularly those used in the manufacture of tablets, capsules, gel caps, and the like, may include, but are not limited to, binders, diluents/fillers, disintegrants, lubricants, and suspending agents.

In order to prepare oral dosage forms (for example, tablets), excipients, any disintegrant, binders, lubricants, and the like may be added to the various variants disclosed in Table 1, and a composition obtained therefrom may be compressed. If necessary, the compressed product may be coated in known methods for taste masking or dissolution or sustained release in the intestine.

Other physiologically acceptable compounds capable of being formulated with the various variants disclosed in Table 1 may include wetting agents, emulsifying agents, dispersing agents, or preservatives which are particularly useful for preventing growth or action of microorganisms. The excipients may be used in a sterile and contaminant-free state.

The various variants disclosed in Table 1 may be incorporated into formulations for cosmetic use and topically applied, and may be, for example, formulated as skin creams (for example, face creams) or body lotions, or incorporated into cosmetics, sunscreens, or moisturizers.

In addition, the various variants disclosed in Table 1 may be incorporated into formulations optionally further including fillers, moisturizers, vitamins (for example, vitamin E), and/or colorants/dyes.

Suitable injectable cosmetic formulations may unlimitedly include at least one filler material in addition to the various variants disclosed in Table 1 but are not limited thereto. Examples of injectable cosmetic wrinkle fillers may include temporary (absorbable) fillers such as collagen (for example, synthetic collagen, bovine collagen, porcine collagen, human collagen, etc.), hyaluronic acid gel, calcium hydride (typically implanted in the form of a gel), or poly-L-lactic acid (PLLA), etc., but are not limited thereto. The peptides also may be incorporated into injectable cosmetic formulations containing permanent (non-absorbable) fillers. Examples of the "permanent" fillers may include polymethylmethacrylate beads (PMMA microspheres) but are not limited thereto.

The various variants disclosed in Table 1 may be incorporated into or administered with a dermal filler, an injectable formulation, etc. Such an injectable formulation may further include an anesthetic (e.g., lidocaine or an analog thereof). The injectable formulation is substantially sterilized or sterilized and/or conforms to institutional guidelines for subcutaneous injectable fillers.

The various variants disclosed in Table 1 may be administered to a subject by using any route known in the art, wherein the route may be (for example, intravenous, intraperitoneal, subcutaneous, intramuscular, intradermal, or intradermal) injection, inhalation, transdermal application, rectal administration, vaginal administration, or oral administration. Desirable administration routes include subcutaneous, transdermal, or topical application.

Effective amounts of the various variants disclosed in Table 1 may be administered via topical (i.e., non-systemic) administration, for example, peripheral intramuscular, intravascular, and subcutaneous administration, but are not limited thereto.

Administration of the various variants disclosed in Table 1 may be in any convenient manner, for example, by injection, intravenous and arterial stents (including eluting stents), catheter, oral administration, inhalation, transdermal application, rectal administration, and the like.

The various variants disclosed in Table 1 may be formulated with a pharmaceutically acceptable carrier prior to administration, e.g., as described above. The pharmaceutically acceptable carrier may not only be determined by a specific composition to be administered, but may also be partially determined in a specific method for administering the composition.

A dosage administered in a subject, in the context of the methods described in the application, should be sufficient enough to affect a beneficial therapeutic response (for example, increased subcutaneous adipogenesis) in the subject over time. The dosage will be determined by efficacy of an employed specific vehicle/delivery method, administration sites, administration routes, and conditions of the subject, and in addition, a body weight or surface area of the subject to be treated. A size of the dosage will be also be determined by presence of any adverse side effects that accompany the administration of a specific peptide in a specific subject, sex, and an extent thereof.

The various variants disclosed in Table 1 may be administered systemically (e.g., orally or as an injection) according to standard methods that are well known to those skilled in the art. The peptides may be administered to the oral cavity in various forms such as lozenges, aerosol sprays, mouthwashes, coated swabs, and the like. A variety of oral and sublingual formulations also may be considered. The various variants disclosed in Table 1 may be administered as a depot formulation, when formulated as an injection for providing treatment over a period of time.

The various variants disclosed in Table 1 may be administered topically, for example, to the skin surface, local lesions or wounds, surgical sites, or the like.

The various variants disclosed in Table 1 may be delivered through the skin by using a conventional transdermal drug delivery system, i.e., a transdermal "patch", and contained in a layered structure typically serving as a drug delivery device attached to the skin.

Other formulations for topical delivery include ointments, gels, sprays, fluids, and creams, but are not limited thereto. The ointments may be simi-solid preparations, typically based on petrolatum or other petroleum derivatives. Like any other carrier or vehicle, an ointment base should be inert, stable, non-irritating, and non-sensitizing. The creams containing ones selected from the various variants disclosed in Table 1 may be typically viscous liquids, semi-solid emulsions, or often oil-in-water or water-in-oil. Cream bases are typically water washable and contain an oil phase, an emulsifier, and an aqueous phase. Specific ointment or cream bases to be used are provided for optimal drug delivery, as appreciated by those skilled in the art.

The various variants disclosed in Table 1 may be provided as a "concentrate" in a storage container ready for dilution (for example, in a pre-measured volume) or in a soluble capsule ready for adding a large amount of water, alcohol, hydrogen peroxide, or other diluents. For example, the peptide can be lyophilized for later reconstitution.

The various variants disclosed in Table 1 may have various uses. The various variants disclosed in Table 1 may have uses in many applications. For example, since subcutaneous fat provides fullness and firmness to the skin, enhancing formation of the subcutaneous fat is used in plastic surgery procedures. Aging skin contains less subcutaneous fat. Accordingly, one or more of the various variants disclosed in Table 1 according to the present disclosure may be administered to desired sites to promote the formation of the subcutaneous fat and thus accomplish fuller younger-looking skin. This approach may replace current methods of transplanting fat cells from other parts (for example, thighs or buttocks) of the body, which often suffer a low success rate.

The various variants disclosed in Table 1 may be administered, if desired, to enhance subcutaneous adipose tissues (for example, to enhance subcutaneous adipose tissues without substantially increasing visceral fat and/or other adipose tissues). In response to the administration of the various variants disclosed in Table 1, fat cells may be formed in dermal fibroblasts, and a volume thereof may be added in selected subcutaneous sites of the subject.

The various variants disclosed in Table 1 may be used to reduce scarring. This can be achieved by administering one or more of the various variants disclosed in Table 1 in a sufficient amount to reduce scarring and/or the improve appearances around scarring. The scarring may be, for example, scars produced by a burn, surgery, acne, a biopsy, or an injury.

The various variants disclosed in Table 1 may be used in various cosmetic procedures, for example, to improve the appearance of the skin. This may be accomplished by administering one or more peptides to the site of the subject in an amount sufficient to improve the appearance of the skin. Such administration may include subcutaneous administration to regions such as lips, eyelids, cheeks, forehead, chin, neck, and the like. The peptides are used in the methods of reducing wrinkles, lifting sagging skin, improving the surface texture of the skin, removing or filling the wrinkles, removing or reducing aged spots, and/or removing dark circles under eyes. These cosmetic applications are exemplary and are not intended to be limiting.

The various variants disclosed in Table 1 may be used to improve a tissue volume at the site of a subject. This may be accomplished by administering one or more of the peptides described herein to the site of the subject in an amount sufficient to increase tissue volume. For example, the increase in the tissue volume may include firming or augmenting breast tissues and/or firming or augmenting hip tissues or other parts of the body or face.

The FGF2 used at this time may be used in an amount of 0.01 to 10 ppm. When the FGF2 is used in an amount of greater than or equal to 10 ppm, side effects to induce adverse reactions may occur due to the excessive amount. Accordingly, the FGF2 may be used within a practical use range of 0.01 ppm to 10 ppm, and preferably, 0.01 ppm to 2 ppm.

The various variants disclosed in Table 1 may also be used to soften the skin in the site of a subject. This may be accomplished by administering one or more of the peptides described herein to the desired site in an amount sufficient to soften the skin. The softening the skin may include smoothing scars caused by acne, smoothing out a cellulite region, smoothing or reducing stretch marks, and/or smoothing out wrinkles.

The various variants disclosed in Table 1 may be used to recruit stem cells to the formation of subcutaneous fat in a subject. This may be accomplished by administering the various variants disclosed in Table 1 in an amount sufficient to recruit stem cells for forming subcutaneous fat. This has utility, for example, in various reconstructive surgical procedures and the like.

The various variants disclosed in Table 1 may be used to reconstruct tissue in a subject. Such reconstruction may include, for example, breast reconstruction (e.g., after surgery to remove a tumor), or face or limb reconstruction (e.g., after an automobile accident or burn). This may be achieved by administering the various variants disclosed in Table 1 in an amount of increasing the tissue volume either during or after the tissue reconstruction process. The various variants disclosed in Table 1 may optionally be used in combination with tissue graft materials or other procedures that enhance healing of the skin or injured tissues.

The various variants disclosed in Table 1 may be used to reduce heel pain experienced by a subject when walking by administering it in a sufficient amount.

The various variants disclosed in Table 1 may be administered for augmentation of subcutaneous fat to increase thermoregulation and/or improve the immune function. The subject may be treated with the various variants disclosed in Table 1 to prevent disease or treat ongoing diseases associated with increased organ fat unlimitedly including cardiovascular disease, and other obesity associated diseases.

Administration in any of these methods may be topical or systemic, and may be by any route described herein, such as topical, subcutaneous, transdermal, oral, nasal, vaginal, and/or rectal administration. Preferably, the various variants disclosed in Table 1 may be administered by subcutaneous injection. Alternatively, the various variants disclosed in Table 1 may be administered topically in the form of a skin cream such as a face cream, or may be administered transdermally through a transdermal patch.

Although the above uses and methods are described with reference to use in humans, they are also suitable for use in animals, e.g., for veterinary use. Accordingly, certain preferred organisms include, but are not limited to, humans, non-human primates, canines, horses, cats, pigs, ungulates, rabbits, and the like.

Medium

The various variants disclosed in Table 1 are included in a 'medially effective amount' corresponding to the amount necessary to maintain the pluripotent stem cells in an undifferentiated state for at least 5 passages to provide a human pluripotent stem cell medium.

In the present disclosure, the term 'human pluripotent stem cells', which includes both human embryonic stem cells and induced pluripotent stem cells, refers to an ability to form a pluripotency that allows it to generate the same progeny and virtually all cell types in the human body self-renewal capacity.

In the present disclosure, the term "maintaining stem cells in a pluripotent state" means maintaining the cells in an undifferentiated state having an ability to differentiate into virtually any cell type. This pluripotent state depends on a stemness-supporting cocktail of growth factors, of which FGF2 is the most important growth factor. FGF2 supports self-renewal in several ways: directly activating the mitogen-activated protein kinase pathway and indirectly catalyzing transforming growth factor $\beta 1$ and activin signaling (Greber, et al. 2008, Stem Cells 25, 455-464). FGF2 contributes in multiple ways to the pluripotency of human PSCs through cell adhesion and survival functions.

The present disclosure provides a method for characterizing an engineered subject FGF2, demonstrating a substitution effect in a protein, a method of using the protein in culturing human PSCs, and a medium including one or more thermostable FGF2 proteins described herein suitable for culturing human PSCs in an undifferentiated state. a medium including one or more thermostable FGF2 proteins described herein is suitable for culturing human PSCs in an undifferentiated state. Human embryonic stem cells (ESCs) used in the examples provided herein were derived from blastocyst embryos obtained with the informed consent of a physician. A well-characterized human ESC cell line (Adewumi, et al. 2007, Nat Biotechnol 25, 803-816) CCTL14 (Center of Cell Therapy Line) at passages 29-41 was used. The well-characterized human ESC cell line CCTL14 was used.

As in human induced pluripotent stem cells (iPSCs), the AM13 cell line, derived using reprogramming of dermal fibroblasts by Yamanaka's cocktail and Sendai virus transfection, was used as passage 34-41 (Kruta et al. 2014, Stem Cells and Development 23, 2443-2454).

Hereinafter, preferred experimental examples are presented to aid the understanding of the present invention, but the following experimental examples are only illustrative of the present invention, and the scope of the present invention is not limited to the following examples.

Experimental Example 1: Construction, Purification, and Thermal Stability Analysis of Variants Using the pQE80 Vector Variants at one position (S137P) and two positions (D28E, S137P) of FGF2 were synthesized and subcloned into a pQE80L vector with a His-Tag. The recombinant vector into which FGF2 was inserted was transformed into Rosetta (DE3)pLysS cells and expressed.

10 ml LB media (Ambrothia) (0.25 g used) was inoculated, and 10 ul of ampicillin (50 mg/ml) was added and then pre-cultured at 37° C.

10 ml of the pre-culture solution and 1 ml of ampicillin (50 mg/ml) were inoculated into 1L LB media (Ambrothia) (25 g used) and cultured at 37° C. When the value of OD600 was 0.6, the culture medium was cooled in a refrigerator at 4° C. for 10 minutes, and then 0.5 mM of beta-di-1-thiogalactopyranoside (β-D-1-thiogalactopyranoside; IPTG) was added to obtain E. coli cells induced for expression at 20° C. for 20 hours.

The expressed pQE80_FGF2 was dissolved in a lysis buffer solution (20 mM Tris pH 8.0, 200 mM NaCl, 3 mM DTT), sonicated, and centrifuged at 13000 r.p.m for 30 minutes, followed by purification.

After centrifugation, the optimally dissolved supernatant was injected into a column with heparin beads. The pQE80_FGF2 protein was washed with a first wash buffer (20 mM Tris pH 8.0, 200 mM NaCl, 3 mM DTT) and a second wash buffer (20 mM Tris pH 8.0, 500 mM NaCl, 3 mM DTT) which are equal to three times the volume of pET17b_FGF2 protein injected into the column, and eluted with 60 ml of an elution buffer (20 mM Tris pH 8.0, 1800 mM NaCl, 3 mM DTT) for primary purification.

Finally, the pQE80_FGF2 protein fraction was purified by gel filtration using a HiLoad™ 16/60 Superdex 75 (Amersham Biosciences) column and a 1×PBS buffer (137 mM NaCl, 2.7 mM KCl, 10 mM $Na_2HPO_4$, 2 mM $KH_2PO_4$, pH 7.4) (WELGENE).

Purified FGF2 proteins were reacted for 0, 2, 4, and 6 days at 37° C. at a concentration of 0.5 mg/ml using the 1×PBS buffer as a basic solution, and were stained with a Coomassie blue staining reagent and subjected to 15% SDS-PAGE electrophoresis. The results are illustrated in FIG. 1.

Figure 1:
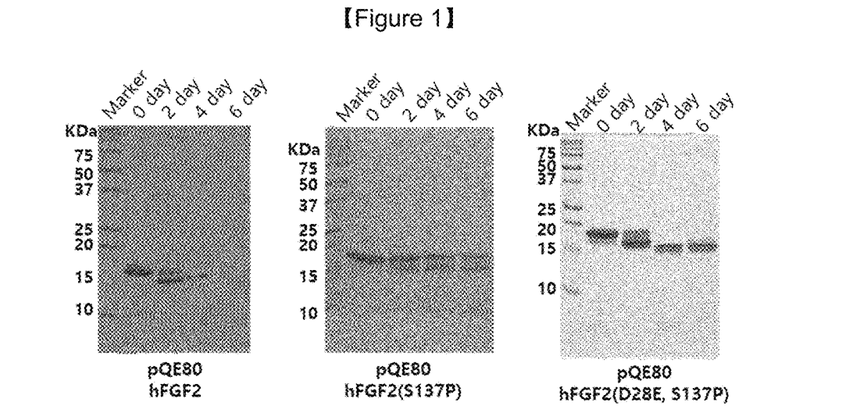
FIG. 1 shows SDS-PAGE of wild-type FGF2 and FGF2 variants (pQE80_hFGF2 (S137P), pQE80_hFGF2 (D28E, S137P)).

As illustrated in FIG. 1, it was confirmed that both mutated polypeptides (pQE80_hFGF2 (S137P), pQE80_hFGF2 (D28E, S137P)) showed improved stability on SDS-PAGE compared to the unmutated hFGF2 (wild-type) polypeptide from FGF2 polypeptide bands identified by 15% SDS-PAGE.

Experimental Example 2: Construction, Purification, and Thermal Stability Analysis of Variants Using the pET17b Vector Variants at 1 position (S137P), mutation at 2 positions (D28E, S137P), and mutation at 4 positions ((D28E, C78L, C96I, S137P), (D28E, C78L, C96W, S137P), (D28E, C78I, C96I, S137P), (D28E, C78I, C96W, S137P)) were synthesized and subcloned into a pET17b vector with His. The recombinant vector into which FGF2 was inserted was transformed into Rosetta (DE3)pLysS cells and expressed.

10 ml LB media (Ambrothia) (0.25 g used) was inoculated, and 10 ul of ampicillin (50 mg/ml) was added and then pre-cultured at 37° C.

10 ml of the pre-culture solution and 1 ml of ampicillin (50 mg/ml) were inoculated into 1L LB media (ambrothia) (25 g used) and cultured at 37° C. When the value of OD600 was 0.6, the culture medium was cooled in a refrigerator at 4° C. for 10 minutes, and then 0.5 mM of beta-di-1-thiogalactopyranoside (β-D-1-thiogalactopyranoside; IPTG) was added to obtain E. coli cells induced for expression at 20° C. for 20 hours.

The expressed pET17b_FGF2 was dissolved in a lysis buffer solution (20 mM Tris pH 8.0, 200 mM NaCl, 3 mM DTT), sonicated, centrifuged at 13000 r.p.m for 30 minutes, and then purified.

After centrifugation, the optimally dissolved supernatant was injected into a column with Heparin beads. The pET17b_FGF2 protein was washed with a first wash buffer (20 mM Tris pH 8.0, 200 mM NaCl, 3 mM DTT) and a second wash buffer (20 mM Tris pH 8.0, 500 mM NaCl, 3 mM DTT) which are equal to three times the volume of pET17b_FGF2 protein injected into the column, and eluted with 60 ml elution buffer (20 mM Tris pH 8.0, 1800 mM NaCl, 3 mM DTT) for primary purification.

The variants of 4 positions were purified by an affinity chromatography method using a solution prepared to not contain 3 mM DTT in both the buffer and the elution buffer.

Finally, the pET17b_FGF2 protein fraction was purified by gel filtration using a HiLoad™ 16/60 Superdex 75 (Amersham Biosciences) column and 1×PBS buffer (137 mM NaCl, 2.7 mM KCl, 10 mM $Na_2HPO_4$, 2 mM $KH_2PO_4$, pH 7.4), (WELGENE).

37° C. Stability Experiment

Purified FGF2 proteins were reacted for 0, 3, 6, and 9 days at 37° C. at a concentration of 0.5 mg/ml using the 1×PBS buffer as a basic solution, and were stained with a Coomassie blue staining reagent and subjected to 15% SDS-PAGE electrophoresis. The results are illustrated in FIG. 2.

Figure 2:
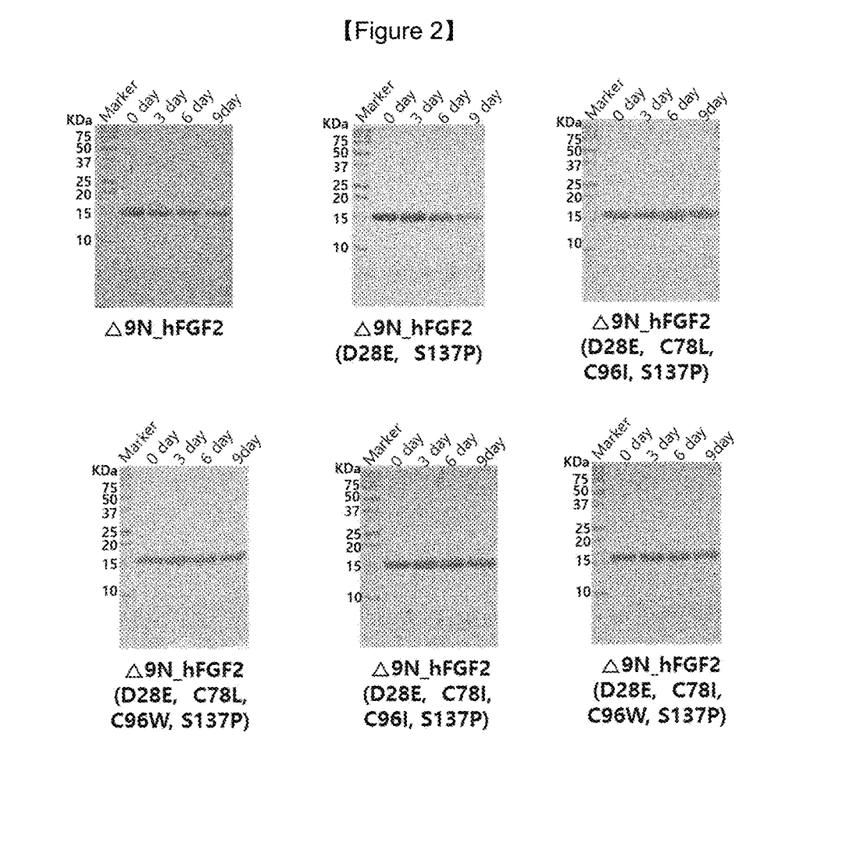
FIG. 2 shows SDS-PAGE for measuring the stability at 37° C. of wild-type FGF2 (Δ9N-hFGF2) and FGF2 variants (Δ9N-hFGF2 (D28E, S137P), Δ9N-hFGF2 (D28E, C78L, C96I, S137P), Δ9N-hFGF2 (D28E, C78I, C96I, S137P), Δ9N-hFGF2 (D28E, C78L, C96W, S137P), and Δ9N-hFGF2 (D28E, C78I, C96W, S137P)).

As illustrated in FIG. 2, it can be seen that the thermal stability of the variants was improved from the FGF2 polypeptide bands identified through 15% SDS-PAGE.

For density measurement, the density of the SDS-PAGE gel was measured using the imageJ program (Wayne Rasband). The results are shown in Table 2.

TABLE 2

| Variants | 0 days | 3 days | 6 days | 9 days |
|---|---|---|---|---|
| Δ9N_hFGF2 | 100 | 84 | 69 | 65 |
| Δ9N_hFGF2 (D28E, S137P) | 100 | 100 | 65 | 17 |
| Δ9N_hFGF2 (D28E, C78L, C96I, S137P) | 100 | 86 | 102 | 89 |
| Δ9N_hFGF2 (D28E, C78I, C96I, S137P) | 100 | 98 | 102 | 103 |
| Δ9N_hFGF2 (D28E, C78L, C96W, S137P) | 100 | 99 | 96 | 94 |
| Δ9N_hFGF2 (D28E, C78I, C96W, S137P) | 100 | 112 | 92 | 65 | unit: %

From the results in Table 2, it can be seen that the variants at 4 positions have improved thermal stability compared to wild-type hFGF2. In particular, it can be seen that Δ9N-hFGF2 (D28E, C78L, C96I, S137P), Δ9N-hFGF2 (D28E, C78L, C96W, S137P), and Δ9N-hFGF2 (D28E, C78I, C96I, S137P) showed relatively improved thermal stability compared to other variants.

45° C. Stability Experiment

Purified FGF2 proteins were reacted for 0, 1, 2, 3, 4, 5, and 6 days at 45° C. at a concentration of 0.5 mg/ml using a 1×PBS buffer as a basic solution, and were stained with a Coomassie blue staining reagent and subjected to 15% SDS-PAGE electrophoresis. The result is illustrated in FIG. 3.

Figure 3:
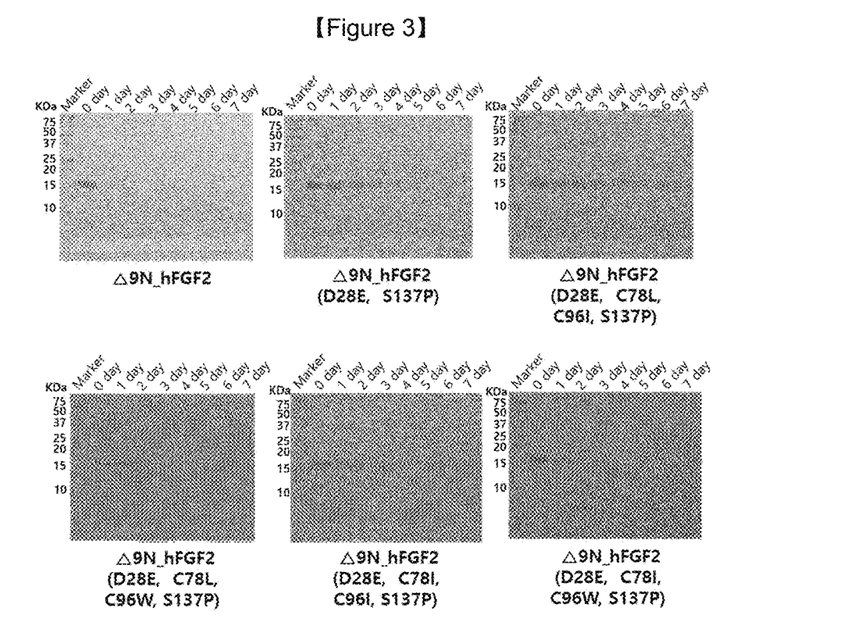
FIG. 3 shows SDS-PAGE for measuring the stability at 45° C. of wild-type FGF2 (Δ9N-hFGF2) and FGF2 variants (Δ9N-hFGF2 (D28E, S137P), Δ9N-hFGF2 (D28E, C78L, C96I, S137P), Δ9N-hFGF2 (D28E, C78I, C96I, S137P), Δ9N-hFGF2 (D28E, C78L, C96W, S137P), and Δ9N-hFGF2 (D28E, C78I, C96W, S137P)).

As illustrated in FIG. 3, it can be seen that the thermal stability of the variants was improved from the FGF2 polypeptide bands identified through 15% SDS-PAGE.

For density measurement, the density of the SDS-PAGE gel was measured using the imageJ program (Wayne Rasband). The results are shown in Table 3.

37° C. for 0, 2, 4, and 6 days, respectively, and cell proliferation activity changes were confirmed.

Figure 4:
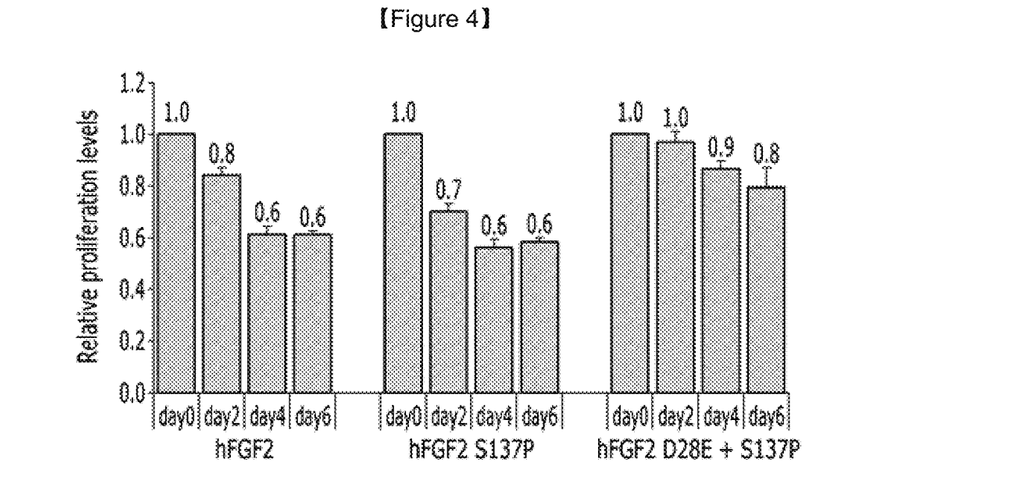
FIG. 4 is a graph measuring changes in cell proliferation activity at 37° C. of wild-type FGF2 and FGF2 variants (pQE80_hFGF2 (S137P), pQE80_hFGF2 (D28E, S137P)).

The results are illustrated in FIG. 4. Referring to FIG. 4, hFGF2 exhibited reduced activity under 2 days' storage at 37° C., and after 4 days' storage at 37° C., only 60% of protein activity of that of 0 day was observed. On the contrary, hFGF2 S137P variants exhibited much more reduced activity under 2 days' storage at 37° C. than hFGF2 and under 4 days' storage at 37° C., and 60% of protein activity of that of 0 day at 37° C. was observed. On the other hand, hFGF2 D28E+S137P variants exhibited more reduced activity, when stored for more days at 37° C. but much less reduced activity than the hFGF2 and hFGF2 S137P variants.

Experimental Example 4: Confirmation of Cell Proliferation Ability of Variants Using pET17b Vector For the variants prepared in the same manner as in Experimental Example 2, BALB3T3 cells were used, and

TABLE 3

|  | 0 days | 1 day | 2 days | 3 days | 4 days | 5 days | 6 days | 7 days |
| --- | --- | --- | --- | --- | --- | --- | --- | --- |
| Δ9N_hFGF2 | 100 | 0 | 0 | 0 | 0 | 0 | 0 | 0 |
| Δ9N_hFGF2 (D28E, S137P) | 100 | 73 | 54 | 37 | 17 | 9 | 3 | 2 |
| Δ9N_hFGF2 (D28E, C78L, C96I, S137P) | 100 | 93 | 62 | 41 | 38 | 16 | 22 | 15 |
| Δ9N_hFGF2 (D28E, C78L, C96W, S137P) | 100 | 76 | 20 | 5 | 0 | 0 | 0 | 0 |
| Δ9N_hFGF2 (D28E, C78I, C96I, S137P) | 100 | 84 | 72 | 54 | 49 | 38 | 35 | 31 |
| Δ9N_hFGF2 (D28E, C78I, C96W, S137P) | 100 | 58 | 21 | 15 | 0 | 0 | 0 | 0 |

From the results in Table 3, it can be seen that all variants have improved thermal stability compared to wild-type hFGF2. In particular, it can be seen that Δ9N-hFGF2 (D28E, C78L, C96I, S137P) and Δ9N-hFGF2 (D28E, C78I, C96I, S137P) have relatively better thermal stability compared to other variants.

Experimental Example 3: Confirmation of Cell Proliferation Ability of Variants Using pQE80 Vector For the variants prepared in the same manner as in Experimental Example 1, BALB3T3 cells were used, and were cultured and maintained in a DMEM medium containing 10% bovine serum. In order to confirm the cell proliferation activity by FGF2, the cells were cultured in an F12/DMEM medium containing 10 ug/ml of insulin, 1 uM of dexamethasone, 10 ug/ml of transferrin, 10 ng/ml of sodium selenite, 100 ug/ml of ovalbumin, and 5 ug/ml of fibronectin.

Cells were cultured in 96 well plates at $0.5 \times 10^4$/well, and treated with FGF2 (0.3 ng/ml) together with heparin (10 ug/ml) for 42 hours. Cell number increase was confirmed by measuring the production level of WST-8 formazan formed by an electron mediator and intracellular dehydrogenases, using WST-8 [2-(2-methoxy-4-nitrophenyl)-3-(4-nitrophenyl)-5-(2,4-disulfophenyl)-2H-tetrazolium, monosodium salt]. The degree of WST-8 formazan production can be confirmed through absorbance (450 nm). The experiment was repeated 3 times, and it was expressed as 'mean±standard deviation'. FGF2 proteins were stored at where cultured and maintained in a DMEM medium containing 10% bovine serum. In order to confirm the cell proliferation activity by FGF2, the cells were cultured in a F12/DMEM medium containing 10 ug/ml of insulin, 1 uM of dexamethasone, 10 ug/ml of transferrin, 10 ng/ml of sodium selenite, 100 ug/ml of ovalbumin, and 5 ug/ml of fibronectin.

Cells were cultured in a 96-well plate at $0.5 \times 10^4$/well, and treated with FGF2 (0.3 ng/ml) together with heparin (10 ug/ml) for 42 hours. Cell number increase was confirmed by measuring the production level of WST-8 formazan formed by an electron mediator and intracellular dehydrogenases, using WST-8 [2-(2-methoxy-4-nitrophenyl)-3-(4-nitrophenyl)-5-(2,4-disulfophenyl)-2H-tetrazolium, monosodium salt]. The degree of WST-8 formazan production can be confirmed through absorbance (450 nm). The experiment was repeated 3 times, and it was expressed as 'mean±standard deviation'. FGF2 proteins were stored at 37° C. for 0, 3, 6, 9, and 12 days, respectively, and cell proliferation activity changes were confirmed.

Figure 5:
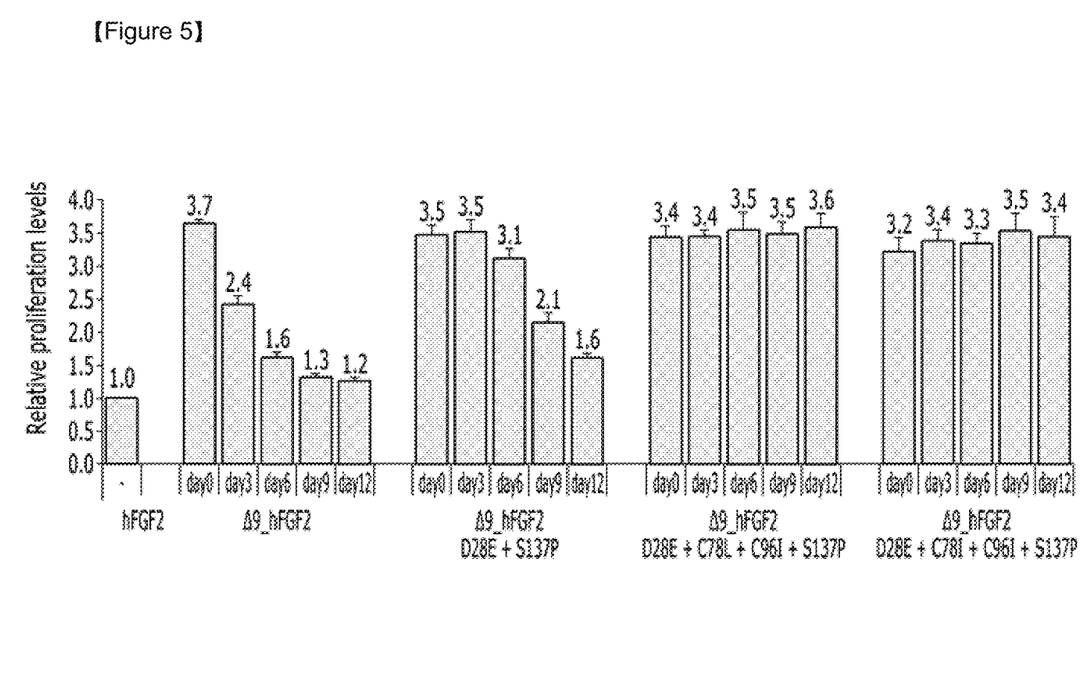
FIG. 5 is a graph measuring changes in cell proliferation activity at 37° C. of wild-type FGF2 (Δ9N-hFGF2) and FGF2 variants (Δ9N-hFGF2 (D28E, S137P), Δ9N-hFGF2 (D28E, C78L, C96I, S137P), and Δ9N-hFGF2 (D28E, C78I, C96I, S137P)).

The results are illustrated in FIG. 5. Referring to FIG. 5, it was confirmed that Δ9_hFGF2 (wild-type) showed reduced activity under the condition of storage at 37° C. for 3 days, and almost lost activity after 6 days of storage at 37° C. The Δ9_hFGF2 D28E+S137P variant showed longer activity than the wild-type protein, and showed a decrease in activity after 9 days of storage at 37° C. Unlike these, the Δ9_hFGF2 D28E+C78L+C96I+S137P mutation protein and the Δ9_hFGF2 D28E+C78I+C96I+S137P variant showed no decrease in activity even under the storage condition of 37° C. for 12 days. Therefore, it was confirmed that the protein activity was stably maintained at 37° C. in the variants according to the examples.

Figure 6:
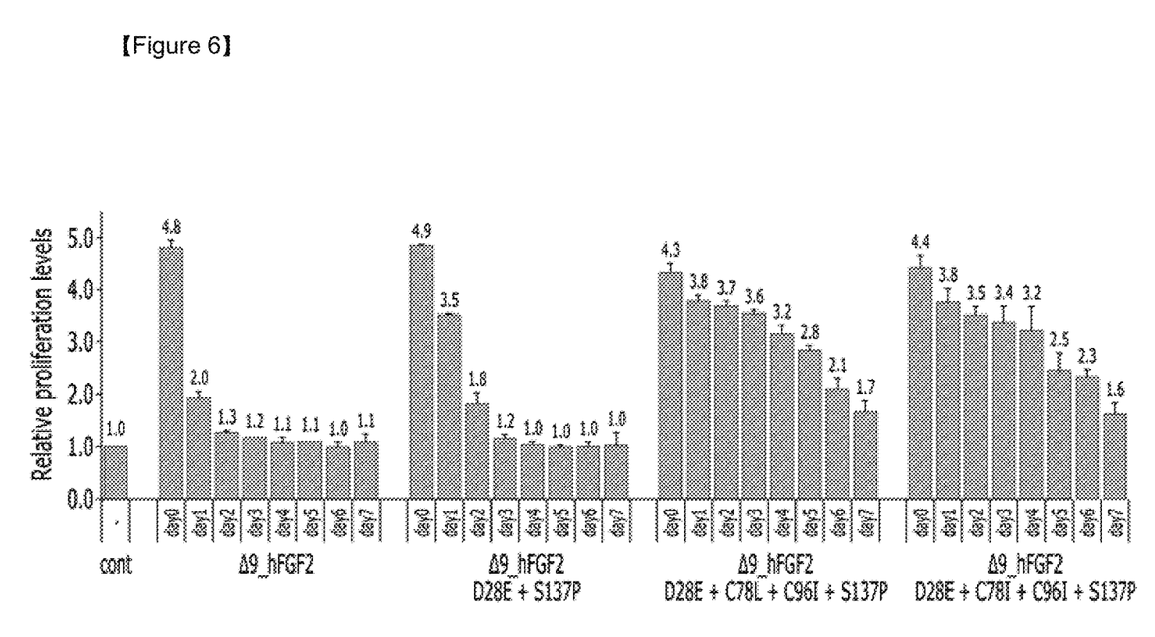
FIG. 6 is a graph measuring changes in cell proliferation activity at 42° C. of wild-type FGF2 (Δ9N-hFGF2) and FGF2 variants (Δ9N-hFGF2 (D28E, S137P), Δ9N-hFGF2 (D28E, C78L, C96I, S137P), and Δ9N-hFGF2 (D28E, C78I, C96I, S137P)).

FGF2 proteins were stored at 45° C. for 0, 1, 2, 3, 4, 5, 6, and 7 days, respectively, and cell proliferation activity changes were confirmed. The results are illustrated in FIG. 6. Referring to FIG. 6, it was confirmed that the Δ9_hFGF2 (wild-type) showed a sharp decrease in activity from 45° C. storage for 1 day, and almost lost activity from 45° C. storage for 2 days. The Δ9_hFGF2 D28E+S137P mutation protein showed a result that the activity was observed longer than the wild-type protein, but showed a result that the activity decreased after storage for 2 days at 45° C. Unlike these, it was confirmed that the activity of the Δ9_hFGF2 D28E+C78L+C96I+S137P mutation protein and the Δ9_hFGF2 D28E+C78I+C96I+S137P mutation protein decreased slightly depending on the number of storage days at 45° C., but the activity was maintained for a longer time than the wild-type, and twice or more proliferation activity was still maintained even after storage at 45° C. for 6 days. It could be confirmed that the proliferation activity of more than twofold was still maintained even after storage at 45° C. for 6 days.

Experimental Example 5: Confirmation of Resistance to Protease Cleavage of Variants Using pET17b Vector Resistance to protease cleavage of Δ9_hFGF2 (wild-type) and the Δ9_hFGF2 D28E+C78L+C96I+S137P mutation protein prepared in the same manner as in Experimental Example 2 was measured.

Figure 7:
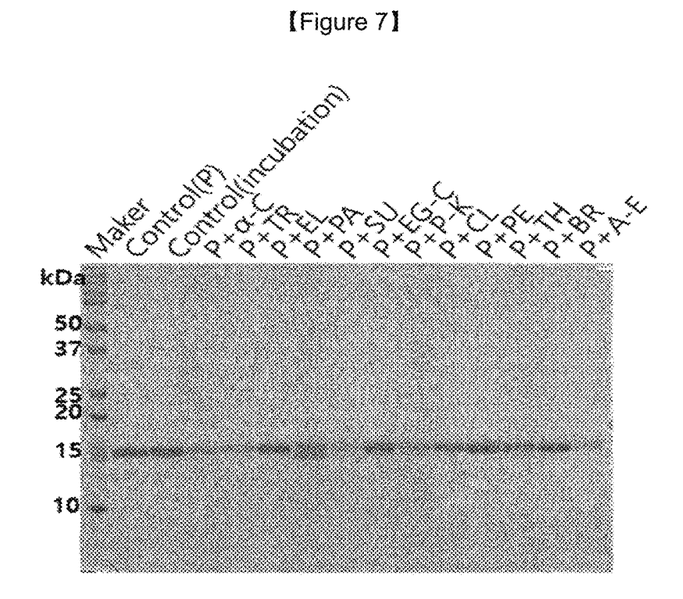
FIG. 7 shows SDS-PAGE for measuring the resistance of wild-type FGF2 (Δ9N-hFGF2) to proteases.
Figure 8:
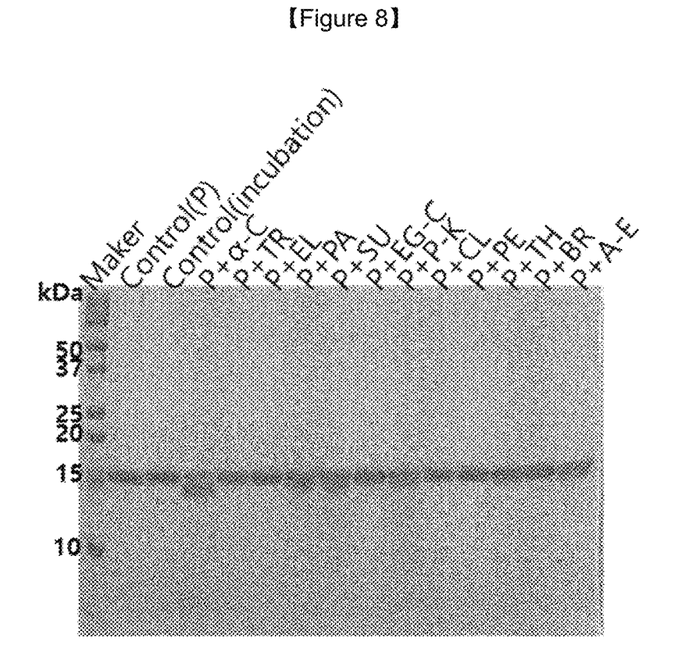
FIG. 8 shows SDS-PAGE for measuring the resistance of the FGF2 variant (Δ9_hFGF2 D28E+C78L+C96I+S137P) to proteases.

FIGS. 7 and 8 show the results of SDS-PAGE measurement of the Δ9_hFGF2 (wild-type) and the Δ9_hFGF2 D28E+C78L+C96I+S137P mutation protein, respectively. In FIGS. 7 and 8, No. 1 is a case measured immediately after protease treatment without incubation, No. 2 is a case measured after protease treatment and incubation at 37° C. for 3 hours, and Nos. 3 to 14 FGF2 0.25 mg/mL show the measurement results after incubation at 37° C. for 3 hours after treatment with 0.0025 mg/mL of each of 12 different types of proteases. Nos. 3 to 14 show the measurement results after Incubation at 37° C. for 3 hours after treatment with 0.0025 mg/ml of each of 12 different types of proteolytic enzymes with respect to FGF2 0.25 mg/mL.

To measure the density of each band, the density of the SDS-PAGE gel was measured using the ImageJ program (Wayne Rasband). The results are shown in Table 4.

TABLE 4

| Nos. | Protease | Δ9_hFGF2 (wild-type) | Δ9_hFGF2 D28E + C78L + C96I + S137P |
|---|---|---|---|
| 1 | X | 100 | 100 |
| 2 | X | 85 | 89 |
| 3 | α-Chymotrypsin (α-C) | 33 | 83 |
| 4 | Trypsin (TR) | 21 | 68 |
| 5 | Elastase (EL) | 70 | 82 |
| 6 | Papain (PA) | 84 | 95 |
| 7 | Subtilisin (SU) | 20 | 79 |
| 8 | Endoproteinase Glu-C (EG-C) | 82 | 93 |
| 9 | Proteinase K (P-K) | 35 | 79 |
| 10 | Clostripain (Endoproteinase-Arg-C) CL | 46 | 85 |
| 11 | Pepsin (PE) | 90 | 84 |
| 12 | Thermolysin (TH) | 47 | 81 |
| 13 | Bromelain (BR) | 85 | 90 |
| 14 | Actinase (A-E) | 11 | 66 |

From the results of FIGS. 7 and 8 and Table 4, the Δ9_hFGF2 D28E+C78L+C96I+S137P mutation protein has overall improved resistance to protease compared to the Δ9_hFGF2 (wild-type). In particular, it can be seen that the resistance for α-chymotrypsin (α-C), trypsin (TR), subtilisin (SU), proteinase K (P-K), clostripain (Endoproteinase-Arg-C) (CL), thermolysin (TH), or actinase (A-E) is relatively significantly improved. Although the various example embodiments have been described above, the scope of the invention is not limited thereto. The embodiments may be implemented in various ways within the scope of the detailed description of the invention and the accompanying drawings, and this also belongs to the scope of the invention.

INDUSTRIAL APPLICABILITY

It may be used in the field of cosmetic or pharmaceutical technology.

The invention claimed is:

1. An FGF2 polypeptide having improved temperature stability compared to wild-type human FGF2 polypeptide, and having FGF activity, comprising the amino acid sequence of SEQ ID NO: 1,
   wherein the aspartic acid (D) at position 28 is replaced by glutamic acid (E),
   the cysteine (C) at position 78 is replaced by isoleucine (I) or leucine (L),
   the cysteine (C) at position 96 is replaced by isoleucine (I), and
   the serine (S) at position 137 is replaced by proline (P).

2. The FGF2 polypeptide according to claim 1, wherein the ccysteine (C) at position 78 is replaced by isoleucine (I).

3. A composition, comprising:
   the FGF2 polypeptide according to claim 1; and
   a pharmaceutically or cosmetically acceptable carrier.

4. A human pluripotent stem cell culture medium, comprising
   the polypeptide according to claim 1 as an active ingredient.

* * * * *